United States Patent [19]

Phillips et al.

[11] 4,304,932
[45] Dec. 8, 1981

[54] PROCESS FOR PRODUCING NOVEL CARBOALKYLATED SURFACE ACTIVE AGENTS AND PRODUCT

[75] Inventors: Brinley M. Phillips; Maurice E. Thompson; Alan J. Lambie, all of Whitehaven, England

[73] Assignee: Albright & Wilson Limited, Warley, England

[21] Appl. No.: 128,410

[22] Filed: Mar. 10, 1980

Related U.S. Application Data

[63] Continuation of Ser. No. 37,107, May 8, 1979, abandoned, which is a continuation of Ser. No. 934,488, Aug. 17, 1978, abandoned.

[30] Foreign Application Priority Data

Aug. 18, 1977 [GB] United Kingdom .............. 34809/77

[51] Int. Cl.$^3$ ................. C07C 101/24; C07C 101/26
[52] U.S. Cl. .................................. 562/561; 562/565; 260/404.5; 252/544
[58] Field of Search ............... 548/352, 354; 562/561, 562/565; 260/404.5

[56] References Cited

U.S. PATENT DOCUMENTS

| | | | |
|---|---|---|---|
| 2,528,378 | 10/1950 | Mannheimer | 548/354 |
| 2,528,380 | 10/1950 | Mannheimer | 548/354 |
| 2,773,068 | 12/1956 | Mannheimer | 548/354 |
| 3,359,275 | 12/1967 | Mannheimer | 548/352 |
| 3,359,275 | 12/1967 | Mannheimer | 548/354 |
| 3,738,996 | 6/1973 | Bloch et al. | 548/354 |
| 4,137,245 | 1/1979 | Christiansen | 548/352 |

FOREIGN PATENT DOCUMENTS 853440 12/1956 United Kingdom .............. 548/354

Primary Examiner—Henry R. Jiles
Assistant Examiner—Jane T. Far
Attorney, Agent, or Firm—Frishauf, Holtz, Goodman & Woodward

[57] ABSTRACT

The reaction of an imidazoline base of the formula:

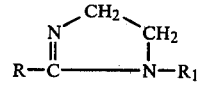

wherein R represents an aliphatic group comprising from 6 to 22 carbon atoms and $R_1$ represents a substituted or unsubstituted alkyl or alkenyl group comprising 1 to 4 carbon atoms, with a carbo-alkylating agent is carried out in two stages. Initially the pH is maintained in the range 7 to 11 and subsequently it is maintained in the range 9 to 12.5. These conditions encourage at least part of the imidazoline to undergo alkylation followed by hydrolysis and further alkylation. The di alkylated amidoamines thus produced are believed to be novel. The reaction products are surfactants which exhibit very low skin irritancy and have a desirably low viscosity. They find particular application in shampoo formulations.

25 Claims, No Drawings

PROCESS FOR PRODUCING NOVEL CARBOALKYLATED SURFACE ACTIVE AGENTS AND PRODUCT

This is a continuation, of application Ser. No. 37,107 filed May 8, 1979, now abandoned which, in turn, is a continuation of Ser. No. 934,488, filed Aug. 17, 1978, now abandoned.

This invention relates to novel chemicals which are produced by a process of carboalkylating certain organic nitrogen containing compounds which have at least one tertiary nitrogen atom as a part of their molecular structure. The products which are amphoteric in nature find use as surface active agents and exhibit unusually low skin-irritancy properties together with a high degree of stability in aqueous media.

In particular this invention is concerned with the products obtained by the interaction of compounds known as imidazolines having the formula

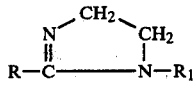

wherein R represents an aliphatic group comprising from 6 to 22 carbon atoms and $R_1$ represents a substituted or unsubstituted alkyl or alkenyl group comprising from 1 to 4 carbon atoms.

U.S. Pat. Nos. 2,528,378 and 2,773,068 describe processes of reacting compounds having the above formula with carbo-and-sulpho-alkylating agents at a pH of 12 or above. The products were represented as being compounds of the formula

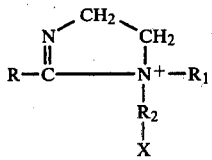

where X represents a carboxylate group $COO^-$, a sulphonate group $SO_3^-$ or a sulphate group $^-OSO_3$ and $R_2$ represents a substituted or unsubstituted alkylene group having from 1 to 4 carbon atoms. However in West German Auslegeschrift No. 1084414 it is suggested that in the conditions used the alkylation is preceded by a hydrolysis reaction yielding a straight chain amido-amine which is then alkylated to give species of the formula

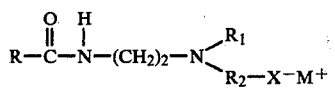

where $M^+$ represents an alkali metal cation e.g. $Na^+$. British Pat. No. 850,514 describes a procedure in which the imidazoline is first hydrolysed and subsequently reacted with a carbo-alylating agent to yield such materials.

British Pat. No. 1,352,770 describes a process in which an imidazoline is reacted with one mole of a carbo-alkylating agent under lower, closely controlled pH conditions so as to favour the alkylation reaction and produce a product which is described as a quaternised imidazoline compound.

Certain of these imidazolines are capable of reaction with more than one molar porportion of a carboalkylating agent. British Pat. No. 853,440 describes the reaction between an imidazoline having the above formula wherein $R_1$ represents a group $-CH_2CH_2OH$ to give compounds which are assigned the formula

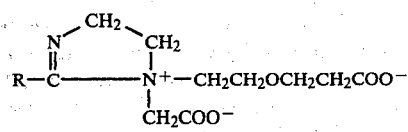

All of these products find use as surfactants and in general they are markedly less irritant to the skin than other conventional surfactants.

From the foregoing discussion it will be appreciated that the nature of the products obtained by the carboalkylation of an imidazoline in an aqueous reaction medium will vary according to the conditions under which the carbo-alkylation reaction is carried out and in particular is dependent upon the pH of the reaction medium. All the prior procedures apparently result in either carbo-alkylation of the imidazoline or hydrolysis of the imidazoline followed by carbo-alkylation.

We have now discovered a novel process of reacting a carbo-alkylating agent with an imidazoline which we believe involves at least a part of the imidazoline undergoing carbo-alkylation to yield an alkylated derivative thereof which then undergoes hydrolysis to form a straight chain amido-amine which in turn undergoes further carbo-alkylation. The product comprises a mixture of novel species apparently derived from this reaction sequence together with other species such as those known as the products produced by the carbo-alkylation either of the imidazoline or of the hydrolysis product thereof. The products exhibit very low skin irritancy properties and provided the reaction is controlled they have a lower viscosity at ambient temperatures than those produced by prior art procedures.

From one aspect our invention provides compounds of the formula

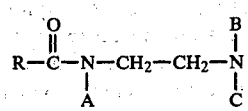

where A represents a group $R_2$-$COO^-$ wherein $R_2$ represents a substituted or unsubstituted alkylene group having from 1 to 4 carbon atoms, or a group $-R_1$ wherein $R_1$ represents a substituted or unsubstituted alkyl or alkenyl group having from 1 to 4 carbon atoms, B and C which may be the same or different, represent groups having the formula $-R_2-COO^-$ or $R_1$ and only one of A, B or C being $R_1$ and where A represents $-R_2-COO^-$ one and only one of B and C may represent a hydrogen atom with the proviso that at least one but only one of A, B or C represents a group $R_1$.

These novel chemicals are produced as the main product of the carbo-alkylating procedures hereinafter described. Separation of the novel compounds from the mixture produced is inconvenient and normally the novel compounds will be employed as surface active agents in admixture with these species.

The product of the carbo-alkylation process will in general terms comprise a mixture of non-carbo alkylated material (wherein neither A, B nor C is $R_3$—COO$^-$); mono-carbo alkylated material (wherein any one of A, B or C is —$R_3$—COO$^-$) and di-carbo alkylated material (wherein any 2 of A, B and C are —$R_3$—COO$^-$). Preferably the reaction will be continued until the active ingredient of the product comprises less than 20% by weight of non carbo-alkylated material. Most preferably the non-carbo alkylated material will comprise less than 10% by weight of the active ingredient of the product. The ratio of mono:di carbo alkylated species in the final product mixture is preferably in the range 1:2.0 to 1:0.2. Most preferably this ratio is in the range 1:1.3 to 1:0.4.

From another aspect our invention resides in a process which comprising treating an imidazoline of the formula

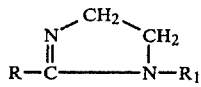

wherein R represents an aliphatic group comprising from 6 to 22 carbon atoms and $R_1$ is as hereinbefore defined with a carbo alkylating agent having the formula Z—$R_2$—COO$^-$ wherein $R_2$ is as hereinbefore defined and Z represents a halogen atom at a temperature of from 40° to 90° C. the pH of the reaction medium being maintained in the range 7.0 to 11.5 and after at least 0.5 moles of carbo-alkylating agent per mole of imidazoline have reacted the pH being maintained in the range 9.0 to 12.0 if necessary after varying the pH; all of the pH's being expressed as the pH of a sample of the reaction mixture diluted so as to bring the solid contents thereof to substantially 10%.

The carbo alkylating agent may be added in its acid form or as a partially neutralised mixture of acid and a salt of that acid. It will be appreciated that throughout this disclosure where a carboxylate group —COO$^-$ is described in its anionic form it may exist as either an acid or a salt thereof or as a zwitterion as appropriate.

The pH of the reaction medium can readily be controlled by regulating the rate of supply of the carbo-alkylating agent or a suitable inorganic base e.g. sodium or potassium hydroxide to the solution.

The overall quantity of carbo-alkylating agent employed in the reaction is at least 1 mole per mole of imidazoline and preferably a quantity of from 2.0 to 4.0 preferably 2.5 to 3.0 moles will be employed. Where less than 2.0 moles are reacted the product will comprise a greater proportion of mono-carbo-alkylated species wherein either B or C represents a hydrogen atom.

The stoichiometry of the reaction to produce the novel products where neither B nor C is hydrogen requires that 2.0 moles of carbo-alkylating agent per mole of imidazoline are reacted and in practice we find that a maximum of 2.0 moles react. Normally between 1.7 and 1.8 moles react. The difference represents the formation of a mono-alkylation product which is incapable of further alkylation and such reactions are suppressed as far as is possible using novel processes. Where surplus of carboxylating agent is used the compounds where B or C is hydrogen will represent only a minor part of the product.

Most preferably the initial reaction between the carbo-alkylating agent and the imidazoline is carried out at a pH of from 9.0 to 10.5 e.g. 9.0 to 10.0.

At lower pH's the progress of the reaction must be monitored more carefully as substantially only one molar proportion of carbo-alkylating agent will react. At a pH of 9 or less very little if any, more than one mole of carbo-alkylating agent will react with the imidazoline where the first part of our process is carried out at these less preferred pH values we prefer to adjust the pH to a value of the range 9 to 12 before 0.8 or more preferably before 0.7 moles or carbo-alkylating agent have reacted. At the higher pH's e.g. 11 to 11.5 an increasing proportion of the imidazoline hydrolyses before carbo-alkylation can take place.

In general where the first stage of the reaction is carried out at the higher end of the pH range the temperature should be maintained at the lower end of the range given e.g. 40° to 70° C. Preferably the temperature of the reaction medium is maintained in the range 50° to 70° C. until 0.5 moles of carbo alkylating agent per mole of imidazoline have reacted. As an empirical guide the maximum pH at which the first stage of the reaction can be carried out successfully at a particular temperature can be estimated using the equation pH max = (200 − temperature in °C.)/13

The reaction can be carried through to completion under these initial preferred pH conditions. However, we prefer to increase the pH after 0.5 or certainly 0.7 or 0.8 moles of carbo-alkylating agent having reacted to a value in the range 9.5 to 12.0 e.g. 10.5 to 12.0.

Preferably during this second stage of the reaction the temperature of the reaction medium is maintained in the range 60° to 80° C.

The whole of the carbo-alkylating agent can be charged into a vessel with the imidazoline before the reaction commences provided careful control of the pH is provided. Alternatively at least 0.7 and preferably a substantially equimolar quantity of the carbo-alkylating agent is charged initially and the remainder is added gradually whilst the initial carbo-alkylation is taking place so as to facilitate the control of the pH.

At the end of the reaction any excess carbo-alkylating agent is hydrolysed so as to form materials which do not interfere with the applications of the novel surface active agents. Thus where the alkylating agent is sodium chloracetate hydrolysis to sodium glycollate and sodium chloride is necessary.

The conditions under the second stage of the reaction is carried out will be chosen so as to complete the carbo-alkylation reaction and this subsequent hydrolysis step within a convenient period say 5 to 25 hours. The desired products will also hydrolyse to a limited extent to give soap. The progress of the reaction should be carefully monitored so as to minimise this loss of product and also to prevent the formation of soap since this causes the viscosity of the product to increase. Despite the innocuous nature of the material formed by hydrolysis of the carbo-alkylating agent the use of a large excess of such a reagent may lead to a product having a high content of these salts which may not be compatible with all the formulations into which the product surfactants may be incorporated. The novel products of our processes can tolerate the presence of surprisingly large quantities of such salts without any substantial increase in viscosity or difficulty in their subsequent utilisation.

This surprising property enable relatively large excess of alkylating agent to be employed in the manufacture of these novel products thus shortening the reaction time. Alternatively a smaller excess can be employed thus producing a product having a lower salt content which will be compatible with formulations which themselves comprise significant quantities of ionic salts.

The immidazoline compounds suitable for use as the starting materials for our novel processes are produced by the reaction between a fatty acid RCOOH and a diamine $H_2NHC_2CH_2NHR_1$ so as to eliminate 2 moles of water therefrom using any of the techniques described in U.S. Pat. Nos. 2,267,965, 2,528,378 and 3,408,361. The fatty acids may be obtained by synthetic means or derived from natural sources. The acids derived from nature comprise a mixture of species which generate a corresponding mixture of imidazolines and derivatives thereof. Such mixtures are useful according to our invention and novel products which comprise species wherein the nature of the group R differs from a part of our invention. Particular fatty acids useful according to our invention include caproic, heptylic, capryllic, undecylic, lauric, palmitic, stearic, isostearic, ethylhexanoic, behenic, arachic, cerotic, oleic, erucic linoleic and ricinoleic.

Natural mixtures useful in our invention include the so called coconut acids, palm oil acids and tallow acids. Preferred acids are those in which the group R comprises an average of from 10 to 18, preferably from 12 to 14 carbon atoms per molecule.

Preferred diamines are those wherein $R_1$ represents an alkyl hydroxyalkyl or amino-alkyl group having from 1 to 4 carbon atoms. Preferably $R_1$ represents a hydroxy-alkyl group comprising from 2 to 4 carbon atoms. Most preferably $R_1$ represents a hydroxyethyl group —$CH_2CH_2OH$.

Preferred carbo-alkylating agents are those in which $R_2$ represents an ethylene or methylene group. The halogen atom is preferably a chlorine atom but may be bromine or iodine. The most preferred carbo-alkylating agent is sodium chloracetate and the reaction is preferably carried out by adding chloracetic acid and sodium hydroxide solutions separately to the reaction medium in order to control the pH thereof.

The novel compounds of the invention and the products of the novel processes of the invention find use as surfactants. Because of their low skin irritancy properties they find special use as ingredients of compositions designed to come into contact with the skin and especially in shampoo compositions used for washing the hair.

The invention is illustrated by the following examples:

EXAMPLE I

A stirred jacketed reaction flask was charged with 197.5 g water and 70.9 g chloroacetic acid, and stirred to dissolve. 204.7 g 1-hydroxyethyl-2-cocoyl imidazoline was added, the temperature being maintained at less than 50° C. A solution of 106.4 g chloroacetic acid in 45.1 g water was added over a period of two hours, the temperature being maintained at 55° C., and the pH at 10.5-11.0 by the addition of sodium hydroxide solution. After a further two hours reaction under these conditions the temperature was increased to 70° C., and the pH to 11.0-11.3 and maintained under these conditions until the sodium chloroacetate was less than 1%. The product had a viscosity of 68 cs, and had the following analysis:
Monoamide—0.6%
Monocarboxymethylated amido amine—11.0%
Dicarboxymethylated amidoamine—14.8%

EXAMPLE II

A solution of 14.2 kg chloroacetic acid in 37.5 kg water was prepared in a stirred, jacketed reactor. 40.9 kg 1-hydroxyethyl-2-cocoyl imidazoline was added, temperature being maintained at less than 50° C. The pH was increased to 9.2 by the addition of 47% sodium hydroxide solution, and the temperature was raised to 55° C. A solution of 21.2 kg chloracetic acid in 9.0 kg water was added over a 2 hr. period the pH being maintained at 9.2–9.4 by the addition of 47% sodium hydroxide solution, and the temperature at 55° C. After a further 2 hrs. reaction under these conditions, when it was found that 0.7 moles chloracetate had reacted per mole imidazoline, the pH was raised to 11–11.2, and the temperature to 70° C., and these conditions were maintained for 17 hrs.

The material was cooled, and the pH was adjusted to 9.1 with hydrochloric acid. It was found by analysis that 1.9 moles chloracetate had reacted per mole imidazoline.

EXAMPLE III

A solution of 18.9 kg chloracetic acid in 50 kg water was prepared in a stirred jacketed reactor. 54.5 kg 1-hydroxyethyl-2-cocoyl imidizoline was added, the temperature being maintained at less than 50° C. The pH was increased to 9.2 by the addition of 47% sodium hydroxide solution, and the temperature was raised to 55° C. A solution of 28.4 kg chloracetic acid in 12 kg of water was added over a 2 hr. period, the pH being maintained at 9.2–9.4 by the addition of 47% sodium hydroxide solution, and the temperature at 55° C. These conditions were maintained for a further 2 hrs. when it was found by analysis that 0.7 moles chloroacetate had reacted per mole imidazoline. The pH was then raised to 10.3–10.5, and maintained at this pH and a temperature of 55° C. for 67 hrs.

It was found by analysis that 1.9 moles chloroacetate had reacted per mole imidazoline. The product of all three process of Examples I to III were clear liquids which exhibited surfactant properties.

EXAMPLE IV

A stirred jacketed reactor was charged with 303 kg chloroacetic acid and 810 kg water, 875 kg 1-hydroxyethyl-2-cocoyl imidazoline was added, the temperature being maintained at less than 50° C. A solution of 455 kg of chloroacetic acid in 193 kg water was added over a period of two hours, the temperature being maintained at 55° C., and the pH at 9.0–9.5. After a further two hours reaction under these conditions the temperature was increased to 70° C., and the pH to 11.0–11.3, and maintained under these conditions for twelve hours until the sodium chloroacetate was less than 1%. The product had a viscosity of 100 cs, and had the following anaylsis:
Monoamide—0.4%
Monocarboxymethylated amidoamine—14.0%
Dicarboxymethylated amidoamine—9.3%

EXAMPLE V

A stirred jacketed flask was charged with 236.3 g chloroacetic acid and 310 g water. This solution was partially neutralised with 139.3 g 47% sodium hydroxide solution, and 273 g 1-hydroxyethyl-2-cocoyl imidazoline was added, the temperature being maintained less than 55° C. After 4 hours reaction under these conditions the pH was increased to 11–11.3. After 12 hours reaction under these conditions the sodium chloracetate was less than 1%.

The product had the following analysis:
Monoamide—0.6%
Monocarboxymethylated amido amine—11.4%
Dicarboxymethylated amido amine—10.4%

EXAMPLE VI

In this comparative example a high pH and temperature was used in the first stage.

A stirred jacketed reactor was charged with 70.9 g chloroacetic acid and 187.5 g water, 204.7 g 1-hydroxyethyl-2-cocoyl imidazoline was added maintaining the temperature less than 50° C.

The temperature was increased to 70° C., and the pH was increased to 11–11.3. A solution of 106.4 g chloroacetic acid in 45.1 g water was added at such a rate so as to complete the addition in 2 hours, but during the addition the solution formed a rigid gel, and the preparation was discontinued.

What we claim is:

1. A process for the preparation of a surface active agent comprising a mixture containing mono- and dicarbo-alkylated derivatives of acylated ethylene diamines which comprises treating an imidazoline of the formula

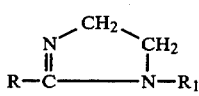

wherein R represents an aliphatic group comprising from 6 to 22 carbon atoms and $R_1$ represents a substituted or unsubstituted alkyl or alkenyl group having from 1 to 4 carbon atoms with from 1 to 4 moles per mole of imidazoline of a carboalkylating agent of the formula $Z-R_2-COO^-$ wherein $R_2$ represents a substituted or unsubstituted alkylene group having from 1 to 4 carbon atoms and Z represents a halogen atom characterized in that the reaction is carried out at a temperature of from 40° to 90° C., the pH of the reaction medium being maintained in the range 7.0 to 11.5 and after at least 0.5 mole of carbo-alkylating agent per mole of imidazoline have reacted the pH of the reaction medium is maintained in the range of more than 9 up to 12.0 to produce said mixture; said mixture having a ratio of said mono- to said di-carbo-alkylated derivatives in the range of from 1:2.0 to 1:0.2 (all pH's being expressed as the pH of a sample of the reaction medium diluted with deionized water so as to bring the solid contents thereof to substantially 10%).

2. A process according to claim 1 wherein $R_1$ represents a hydroxy-alkyl or amino alkyl group having from 1 to 4 carbon atoms.

3. A process according to claim 2 wherein $R_1$ represents a hydroxy ethane group.

4. A process according to claim 1 wherein the group R comprises an average of from 10 to 18 carbon atoms.

5. A process according to claim 2 wherein the group R comprises an average of from 12 to 14 carbon atoms.

6. A process according to claim 2 wherein $R_2$ represents an ethylene or methylene group.

7. A process according to claim 2 characterized in that the carbo-alkylating agent has the formula $Cl-CH_2-COO-$.

8. A process according to claim 1 wherein the pH of the reaction medium is maintained at or below a value given by the equation $$pH\ max = (200 - \text{temperature in °C.})/13$$

until at least 0.5 moles of carbo-alkylating agent per mole of imidazoline have reacted.

9. A process according to claim 6 wherein the pH of the reaction medium is maintained at or below a value given by the equation $$pH\ max = (200 - \text{temperature in °C.})/13$$

until at least 0.5 moles of carbo-alkylating agent per mole of imidazoline have reacted.

10. A process according to claim 1 wherein the temperature of the reaction medium is maintained in the range 50° to 70° C. until at least 0.5 moles of carbo-alkylating agent per mole of imidazoline have reacted.

11. A process according to claim 8 wherein the temperature of the reaction medium is maintained in the range 50° to 70° C. until at least 0.5 moles of carbo-alkylating agent per mole of imidazoline have reacted.

12. A process according to claim 1 wherein the pH of the reaction medium is maintained in the range 9.0 to 10.5 until at least 0.5 moles of carbo-alkylating agent per mole of imidazoline have reacted.

13. A process according to claim 9 wherein the pH of the reaction medium is maintained in the range 9.0 to 10.5 until at least 0.5 moles of carbo-alkylating agent per mole of imidazoline have reacted.

14. A process according to claim 1 wherein after 0.5 moles of carbo-alkylating agent per mole of imidazoline have reacted the pH of the reaction medium is maintained at a value of from 10.5 to 12.0.

15. A process according to claim 14 wherein after 0.7 moles of carbo-alkylating agent per mole of imidazoline have reacted the pH is maintained in the range 10.5 to 12.0.

16. A process according to claim 13 wherein after 0.5 moles of carbo-alkylating agent per mole of imidazoline have reacted the pH of the reaction medium is maintained at a value of from 10.5 to 12.0.

17. A process according to claim 1 wherein after 0.5 moles of carbo-alkylating agent per mole of imidazoline have reacted the temperature of the reaction medium is maintained in the range 60°–80° C.

18. A process according to claim 9 wherein after 0.5 moles of carbo-alkylating agent per mole of imidazoline have reacted the temperature of the reaction medium is maintained in the range 60°–80° C.

19. The surface active agent produced by the process according to any of claims 1, 2, 3, 4, 5, 6, 7, 8, 9, 10, 11, 12, 13, 14, 15, 16, 17 or 18.

20. A composition according to claim 19 which comprises less than 20% by weight of non-carbo-alkylated material.

21. A composition according to claim 20 wherein the ratio of mono carbo-alkylated species to dicarbo-alkylated species is in the range 1:1.3 to 1:0.4.

22. A composition according to claim 21 wherein $R_1$ is a hydroxy-alkyl or amino alkyl group containing from 1 to 4 carbon atoms; the R group contains an average of from 10 to 18 carbon atoms; and $R_2$ is an ethylene or methylene group.

23. A composition according to claim 21 wherein the group R contains an average of from 12 to 14 carbon atoms; and wherein the carbo-alkylating agent has the formula $Cl—CH_2—COO—$.

24. A composition according to claim 23 wherein $R_1$ is a hydroxy ethane group.

25. A surface active agent comprising a mixture containing mono- and di-carbo-alkylated derivatives of acylated ethylene diamines produced by the process which comprises treating an imidazoline of the formula

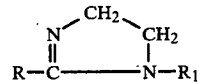

wherein R represents an aliphatic group comprising from 6 to 22 carbon atoms and $R_1$ represents a substituted or unsubstituted alkyl or alkenyl group having from 1 to 4 carbon atoms with from 1 to 4 moles per mole of imidazoline of a carboalkylating agent of the formula $Z-R_2-COO^-$ wherein $R_2$ represents a substituted or unsubstituted alkylene group having from 1 to 4 carbon atoms and Z represents a halogen atom characterized in that the reaction is carried out at a temperature of from 40° to 90° C., the pH of the reaction medium being maintained in the range 7.0 to 11.5 and after at least 0.5 mole of carbo-alkylating agent per mole of imidazoline have reacted the pH of the reaction medium is maintained in the range 9.0 to 12.0 to produce said mixture; said mixture having a ratio of said mono- to said di-carbo-alkylated derivatives in the range of from 1:2.0 to 1:0.2 (all pH's being expressed as the pH of a sample of the reaction medium diluted with deionized water so as to bring the solid contents thereof to substantially 10%).

* * * * *